United States Patent [19]

Liu et al.

[11] Patent Number: 4,835,456

[45] Date of Patent: May 30, 1989

[54] CRYOGENIC DENSITY AND MASS-FLOW MEASUREMENT SYSTEM

[75] Inventors: Frederick F. Liu; Steven W. H. Chow, both of Northridge, Calif.

[73] Assignee: Quantum Dynamics Company, Inc., Woodland Hills, Calif.

[21] Appl. No.: 151,113

[22] Filed: Feb. 1, 1988

[51] Int. Cl.[4] .................. G01R 27/26; G01N 9/00
[52] U.S. Cl. .................. 324/61 R; 73/361.02; 73/361.03; 73/32 R; 364/558
[58] Field of Search .......... 324/71.1, 61 R, 71.5; 73/32 R, 186.01, 861.02, 861.03; 364/558; 62/49

[56] References Cited

U.S. PATENT DOCUMENTS

| | | | |
|---|---|---|---|
| 3,421,077 | 1/1969 | Liu et al. | 324/61 R |
| 3,839,909 | 10/1974 | Sander | 364/558 |
| 3,933,030 | 1/1976 | Forster et al. | 324/61 R |

Primary Examiner—Reinhard J. Eisenzopf
Assistant Examiner—Anthony L. Miele
Attorney, Agent, or Firm—Albert O. Cota

[57] ABSTRACT

A cryogenic density and mass-flow measurement system incorporating a high-speed microprocessor-based cryogenic fluid density instrumentation that is based on the rigorous application of the molecular dielectric theory, using a dielectric susceptibility function in the application of the Clausinus-Mossotti formula, and the introduction of the quantitation of a new susceptibility parameter k which serves to bridge the gap between the theoretically rigorous molecular dielectric equation and the macroscopic dielectric equation. The operating principle is formulated on a differential dielectric measurement approach with a new algorithm which provides for automatic adjustments for polarizability and stray capacitance changes. High precision digital density measurement is achieved over a wide range of cryogenic fluid states ranging from supercritical through subcritical to the slush phase.

17 Claims, 5 Drawing Sheets

CRYOGENIC DENSITY AND MASS-FLOW MEASUREMENT SYSTEM

TECHNICAL FIELD

The invention pertains to the general field of fluid density measurement devices and more particularly to a microprocessor-based system that accurately measures the density of a cryogenic fluid and uses the density measurement with other developed parameters to compute and display cryogenic flow rate, totalized flow data and mass flow.

BACKGROUND ART

The mass flow of a fluid can be determined by measuring its volume flow and applying a density factor to the volume measurement. In the past, an average density was adequate for most applications and separate measurement of density was not required. However, in a propulsion system using cryogenic propellant, such as liquid hydrogen, the density of the cryogenic propellant under steady or transient flow conditions is an important parameter relating to the performance and reliability of the system. Thus, high accuracy of instantaneous density measurement is often required.

The density of a cryogenic fluid in the liquid phase, such as liquid hydrogen follows the equation of the state of the fluid and is primarily a function of temperature, and to a lesser extent, of pressure. This relationship, however, is not always applicable if the fluid is in a two-phase flow containing vapor or supercritical state. The quality of the cryogenic fluid is an additional consideration since vapor content can substantially alter the overall fluid density value.

The theoretical characterization of the fluid density in terms of dielectric constant and refractive index gained impetus in physics due to the Lorentz-Lorentz formulation, and the subsequent developments in dielectric theory due to Onsager, Van Vleck, Froelich, Kirkwood, Langevin-Debye, et al. One dielectric formula which is conspicuously notable in such evaluation is the Clausius-Mossotti equation, despite its early origin and later coexistance with the Onsager formula. The Clausius-Mossotti formula is considered conceptually applicable to non-polar spherical molecules, of which certain liquid gases or cryogenic fluids are examples.

Among the experimental techniques utilizing the dielectric approach, the Clausius-Mossotti ratio has been applied to instrument the density of cryogenic propellents and its multiphase fluid mechanics in aerospace technology. In low temperature physics investigations, high speed analog-type computational dielectric measurement has been applied earlier by researchers to probe into the dynamic phase transitional phenomena of liquid gases, including observations on the period-doubling transients of the bifurcation cascade.

Most of the previously reported methods were either of non-computational or analog computer type design. As such, rigorous applications of pertinent theoretical parameters was neither implemented nor emphasized. However, recent low temperature research—e.g. in the areas of space science, chaos research and liquid hydrogen bubble chamber applications—requires greater conceptual rigor in order to optimize the measurement uncertainties and resolution. The instant invention utilizes a rigorous solution of the molecular Clausius-Mossotti formula by bridging the gap between the macroscopic and molecular dielectric theory using a dielectric susceptibility parameter; and, in combination with a high-speed microprocessor based electronics system to overcome the problems inherent with the current analog measurements.

A search of the prior art did not disclose any patents that read on the claims of the instant invention. However, U.S. Pat. No. 3,421,077, issued Feb. 7, 1969, to Frederick F. Liu, who is also the inventor of the instant invention, is considered related. The U.S. Pat. No. 3,421,077 patent discloses an analog system that measures the density of a cryogenic fluid by sensing the fluid's dielectric properties. The dielectric-to-density converter and electronics of the U.S. Pat. No. 3,421,077 patent differ from the present invention as does the mechanization of the Clausius-Mossotti equation. One noteable difference in the prior art equation is that the proportionally term $\overline{K}$ is treated as a constant, whereas in the instant invention, the $\overline{K}$ term is variable and is compensated by computer solution of the dielectric parameter of $\epsilon - 1$.

DISCLOSURE OF THE INVENTION

The cryogenic mass-flow measurement system is designed for very high precision liquid gas flow rate measurements over wide flow ranges, covering subcritical, supercritical and phase-transitional fluid states. Cryogenic fluids are essentially nonpolar dielectric. Therefore, the density of the fluid is related to the quantitative relation between density and dielectric constants which are based on the Lorentz-Clausius-Mossotti equation as applied to the macroscopic dielectric theory. Lorentz, in his works entitled "Theory of Electronics" attributed the following macroscopic relation to Clausius and Mossotti:

$$\frac{(\epsilon - 1)}{\rho(\epsilon + 2)} = \text{constant} \qquad \text{Eq. 1}$$

where $\epsilon$ is the dielectric constant, $\rho$ the density of non-polar dielectrics.

The above relation implies that the constant is independent of density and temperature. For polar dielectrics, it should be constant as long as the temperature remains constant. However, for non-polar fluids, deviations from the constancy relationship were noticeable. The 'molecular' Clausius-Mossotti formula was then envolved in the following form; it has the same mathematical structure as the macroscopic formula, but of different significance regarding to polarizability:

$$\frac{(\epsilon - 1)}{(\epsilon + 2)} = \frac{\alpha}{a^3} \qquad \text{Eq. 2}$$

Here, the polarizability $\alpha$ is a property of a single molecule independent of the macroscopic parameters, whereby $$\alpha \approx 16\pi \left[ \frac{h^2}{me^2} \right]^3$$

according to the quantum mechanical model. It is related to the quantity p, where $p = 2.52 \times 10^3 \alpha$ is defined as the molecular polarizability. For a spherical model with radius a, the parameter $\frac{4}{3}\pi a^3$ is a quantitative representation of the number of molecules $N_0$ per unit volume, and which is determined by the molecular weight W and the density, so that $$\frac{3}{4\pi a^3} = N_0 = \frac{\rho A}{W},\qquad \text{Eq. 3}$$

where A is Avogadro's number. The Langevin-Debye equation which Van Vleck considers it a good approximation for molecular model, expresses the Clausius-Mossotti ratio in the relationship $$\frac{(\epsilon - 1)}{\rho(\epsilon + 2)} = \frac{\gamma\alpha}{3M} = \text{constant},\qquad \text{Eq. 4}$$

where M is the mass of a molecule, and $\gamma$ is a constant that depends only on the units used. With the introduction of the molecular expression, the equation is rewritten in terms of molecular weight W and the molecular polarizability p, in the following form:

$$p = \frac{W(\epsilon - 1)}{\rho(\epsilon + 2)}\qquad \text{Eq. 5}$$

In dealing with non-polar cryogenic fluids, the significance of p is thus noticeable.

When the use of conventional engineering units for density is suitable, e.g., in lb/ft$^3$, the formula can be written as $$\rho = \kappa \left[\frac{\epsilon - 1}{\epsilon + 2}\right],\qquad \text{Eq. 6}$$

where $\kappa = W/p$.

For cryogenic fluids, published experimental data and theoretical refinement have shown that the proportionality ratio $\kappa$ is not strictly a constant, but varies slightly with the fluid state. Prior to the development of a method for the continuous compensation of such variation in $\kappa$, a constant $\overline{\kappa}$ was used to relate the density and CMR, where $\kappa$ is the mean average of $\overline{\kappa}$ over a given temperature range, for example as tabulated in Table 1.

TABLE 1

PROPORTIONALITY $\overline{K}$ CONSTANTS OF CRYOGENIC FLUIDS

| Cryogenic Fluid | $\overline{K}$(Lb/Ft$^3$) | Applicable Temp. Range |
|---|---|---|
| Liquid Hydrogen | 63.3 | 15–20K |
| Liquid Nitrogen | 383 | 74–100K |
| Liquid Helium | 495 | 2.6–4.0K |
| Liquid Oxygen | 515 | 65–90K |
| Liquid Flourine | 648.9 | 66–89K |

It must nevertheless be pointed out that the densities of cryogenic fluids can undergo dynamic variations under certain thermodynamic variations and flow conditions, even if the fluid temperature remains the same. Consequently and except for stationary state, the fluid temperature cannot be suitably used for practical density measurement, the complexity of which is noticeable from an initial analysis. The values of $\kappa$ for liquid hydrogen used in this analysis are derived by correlating the earlier dielectric data of Guillien (1939) with the fluid properties of hydrogen given by Itterbeek and Paemel (1941); and, with NBS-CEL data of Roder and Goodwin (1961).

In view of the polarizability involvement shown by Equations 2, 4, and 5; the apparent temperature variability of $\kappa$ leads one to focus on the parameter $\epsilon - 1$, rather than $$\frac{(\epsilon - 1)}{(\epsilon + 2)}.$$

This postulation is reached from the following susceptibility equation; that the relation between $\epsilon - 1$ and the density related molecular number N is influenced, among others, by the polarization and dipole moment as well as by low temperature; such that:

$$\epsilon - 1 = \gamma\chi = \gamma N\left(\alpha + \frac{\mu^2}{3KT}\right)\qquad \text{Eq. 7}$$

where $\mu$ is a dipole moment parameter. Accordingly, $(\epsilon - 1)$ is a parameter directly related to dielectric susceptibility $\chi$.

Equation 5 is now re-examined by putting $W/\rho = v$. Where $v$ is the molecular volume, the following function relationship attributed to Kirkwood can be written.

$$\epsilon - 1 = \frac{3P}{v}\left[1 + \frac{P}{v} + \left(\frac{P}{v}\right)^2 + \ldots\right],\qquad \text{Eq. 8}$$

$$\text{if}\ \frac{P \cdot \rho}{W} = \frac{\epsilon - 1}{\epsilon + 2} < 1$$

One notices, even if the deviation of the polarizability p is itself small for hydrogen molecules, according to Stewart; its overall effect can still be significant due to the power series nature of the Kirkwood formula, where $\epsilon - 1$ exhibits a polynominal relationship with density $\rho$ and polarizability p. Since the function is analytic, a computer transformation of $\kappa$ VS $\epsilon - 1$ results in the identification of an original parameter which yields an original functional relationship of the following form:

$$\kappa = A(0) + A(1)[\epsilon - 1] + A(2)[\epsilon - 1]^2 + A(3)[\epsilon - 1]^3 + \ldots$$
$$= \Phi[\epsilon - 1]\qquad \text{(Eq. 9)}$$

$\kappa$ is thus interpreted as a function of the dielectric susceptibility $(\epsilon - 1)$.

The conceptual implication is significant; a susceptibility function, determined through dielectric measurements, is able to integrate the multiplicity of molecular effects due to polarizability and fluid state changes. Its inclusion made possible the retention of the essential simplicity of the Clausius-Mossotti ratio of the macroscopic formula in applications which would require the use of the molecular formula.

The new methodology was evaluated by comparative analysis, taking into consideration the uncertainties of available low temperature hydrogen data. As before, the published thermophysical properties from Itterbeek and Paemel's (1941) work are correlated with the early dielectric data of Guillien (1939), but for comparison only. The resultant $\kappa$VS$\epsilon - 1$ fitting is established by using the latest (1982) NBS data on dielectric and thermophysical properties as compiled by Younglove et al. In each case, however, the functional relationship between $\kappa$ and $\epsilon - 1$ is found to be convergent, and of a polynomial form shown by Eq. 9.

Without further tabulating the lengthy computer processing for hydrogen the 5th-order fitting of Guillien data shows a regression coefficient of 0.9989, or the goodness of the fit is 99.89%. With the extensive data from Younglove et al, the regression coefficient of the 4th-order fit is 0.9993; with

A(0)=6.1002
A(1)=2.4171
A(2)=−2.0510
A(3)=7.5413
A(4)=−9.8955

Thus, the density of non-polar cryogenic fluids can be determined with rigor according to the molecular formula given in Eq. 6; namely, by applying a newly found corrective function of dielectric susceptibility $\Phi(\epsilon - 1)$ in computation with the CMR function. Such a role for the susceptibility factor was not explicitly emphasized earlier in theories; interest where then directed mostly at the fundamental issues of polarizability; and, the absence or presence of short range interaction between molecules. However, the susceptibility parameter $\kappa$, being conceptually meaningful, is more readily applicable than $1/\kappa$. As given in the NBS publications, Younglove cited the following empirical relation, $$1/\kappa(=C_m)=B(1)+B(2)\rho+B(3)\rho^2+B(4)\rho^3+B(5)T+B(6)P$$

The determination of $1/\kappa$ thus requires the knowledge of fluid density $\rho$, temperature T, and pressure P. These three fluid state values are to be simultaneously measurable. The new DDC methodology, however, is based solely on dielectric measurement of which is easier to manage on a real-time basis.

In view of the above mathematical derivation and the use of the formulae in a high-speed microprocessor based design, it is the primary object of the present invention to have a system that will accurately provide the density and mass-flow of a cryogenic fluid over a wide range of fluid states ranging from supercritical through subcritical to solid formation phases.

In addition to the primary object, it is also an object of the invention to provide a system that:
 is rigorous in concept without the excessive complexity in the multiplicity of measurements,
 is reliable and easily maintained,
 is simple to use,
 can be made to be portable, and
 can be made with parts that meet military standards, These and other objects and features of the instant invention will be apparent from the following detailed description, taken with reference to the figures of the accompanying drawings.

BEST MODE FOR CARRYING OUT THE INVENTION

The best mode for carrying out the cryogenic mass-flow measurement system is presented in terms of a preferred embodiment that is designed to accurately measure the density of a cryogenic fluid and to use the density measurement, in combination with other developed computational parameters, to compute and display the cryogenic flow rate.

Figure 1:
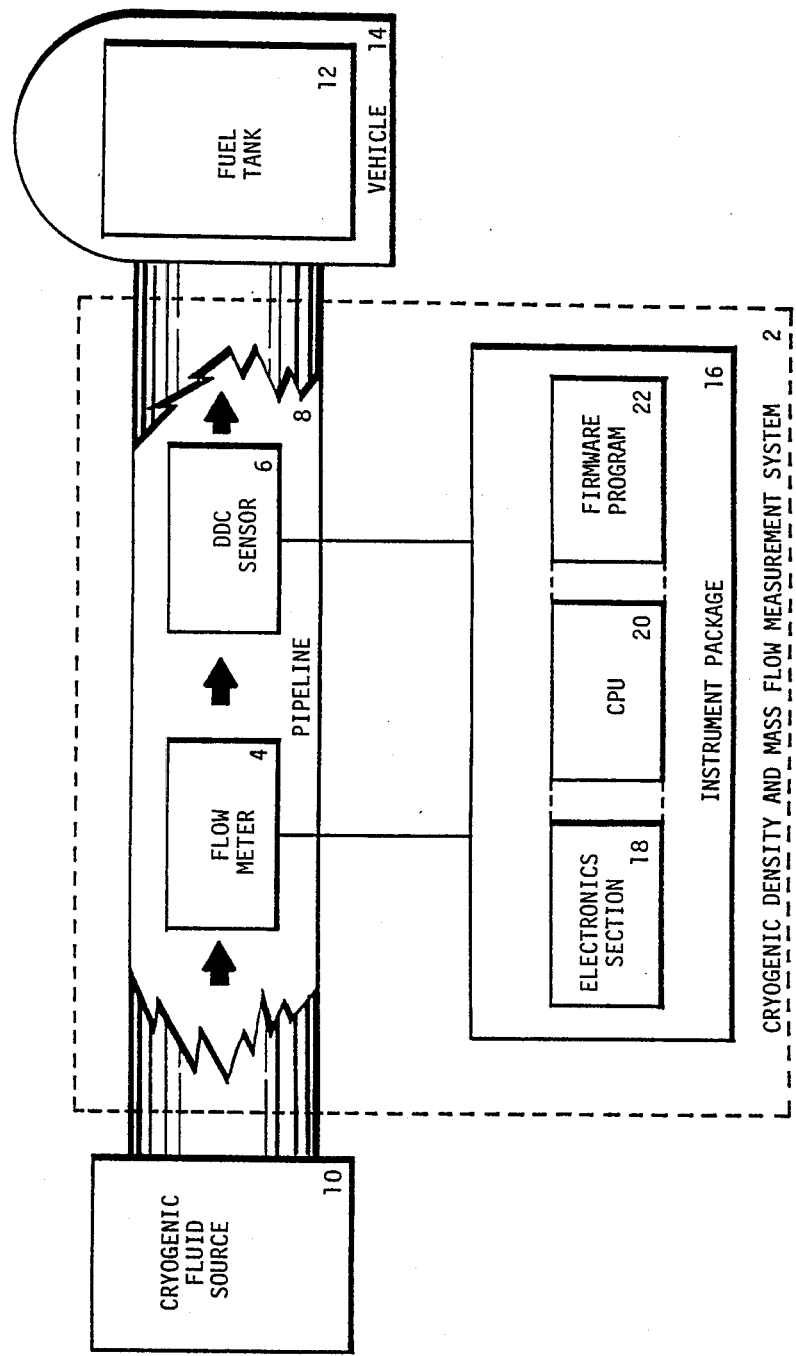
FIG. 1 is a diagrammatic representation showing the cryogenic mass-flow measurement system interfacing with a cryogenic fluid source and a fuel-receiving vehicle.

The system 2, as shown within the dotted lines of FIG. 1, is comprised of a flow meter 4 and a dielectric-to-density converter (DDC) sensor 6 which are connected into a pipeline 8 for supplying cryogenic fluid from a cryogenic fluid source 10 to a fuel tank 12 located in a vehicle 14. The signals from the flow meter 4 and DDC sensor 6 are supplied to an instrument package 16 where the signals operate in combination with an electronics section 18, a CPU (microprocessor) 20 and a firmware program 22 that utilizes the molecular Clausius-Mossotti formula of the dielectric theory to compute the cryogenic fluid density over the subcritical and supercritical phases of the fluid covering both the liquid and vapor phases.

Figure 2:
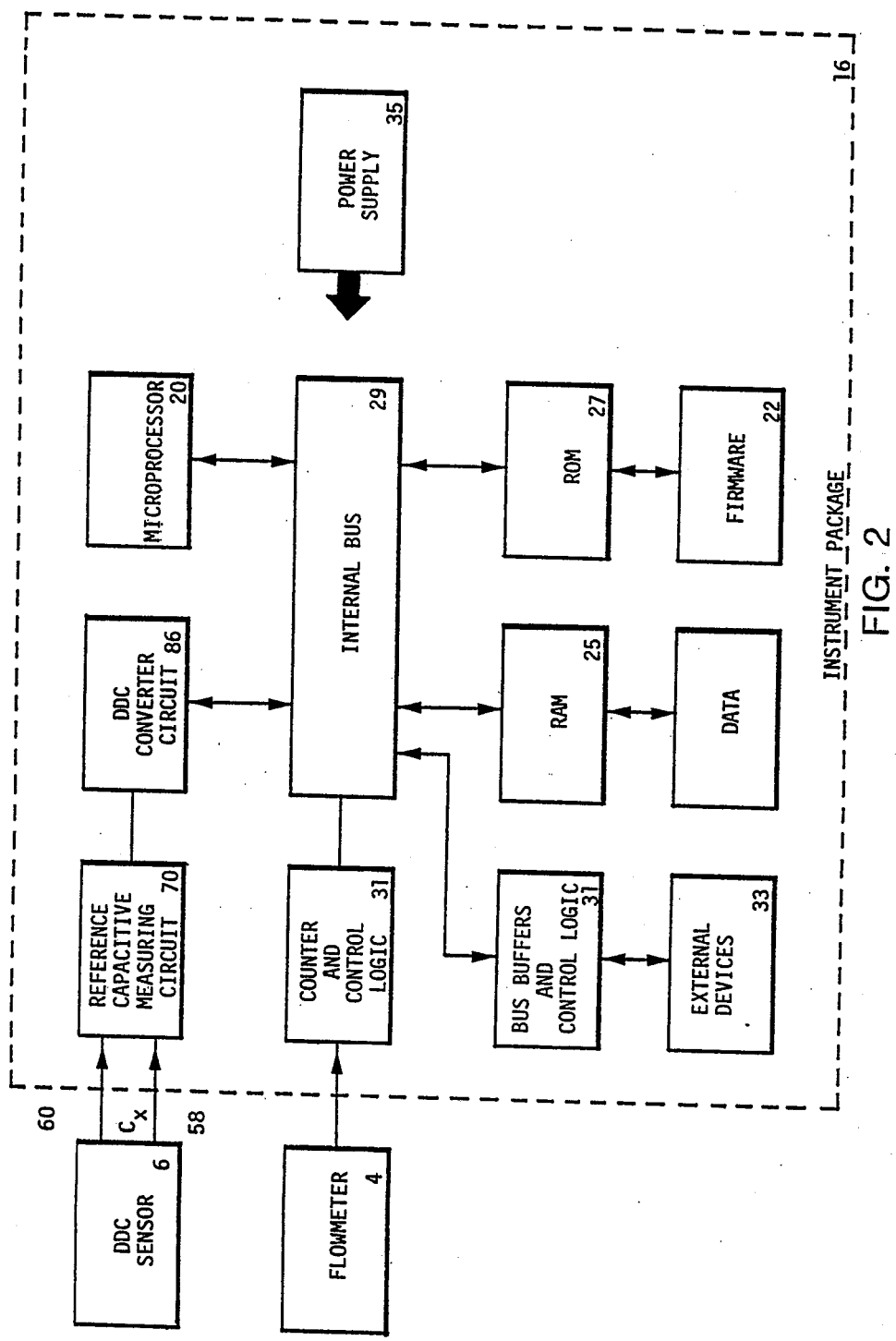
FIG. 2 is an overall block diagram of the cryogenic mass-flow measurement system of FIG. 1.

The operation of the cryogenic mass-flow measurement system 2 can best be understood by referring to the system block diagram of FIG. 2. As shown, the DDC sensor 6 and flow meter 4 supply the input into the instrument package 16. The DDC sensor, which is described in detail infra, supplies a capacitive signal $C_x$. The flow meter 4 senses the rate of fluid flow, as in the pipeline 8 of FIG. 1, and supplies an electrical signal indicative of that flow rate. The flowmeter 4 may be substantially any conventional design and the details thereof do not form a part of the present invention.

The instrument package 16, as shown in FIG. 2, is comprised of ten major elements: an internal bus 29, a referenced capacitive measuring circuit 70, a DDC converter circuit 86, a microprocessor 20, system firmware 22, a counter and control logic circuit 24, a RAM 25, a ROM 27, and a bus buffers and control logic circuit 31.

The internal bus 29 provides the internal interconnection means between selected elements of the instrument package 16. The output of the DDC sensor 6, which consists of the capacitive signal $C_x$, is applied to the referenced capacitive measuring circuit 70. This circuit includes, in part, an oscillator circuit that functions with two capacitors. One capacitor is the DDC capacitor ($C_x$) which is located externally in the DDC sensor and the other is a temperature controlled reference capacitor ($C_r$) having a precisely known capacitance and located within the capacitive measuring circuit 70.

The $C_x$ capacitance is periodically compared with the $C_r$ capacitance. The circuit 70 then converts the $C_x$ capacitance to a proportional frequency signal that is applied to the DDC converter circuit 86. A detailed theory of operation for the referenced capacitive measuring circuit 70 is described infra.

The proportional frequency signal from the sensing circuit 70 is applied to a DDC converter circuit 86 where the signal is converted to a corresponding digital signal. The digital signal is then applied to a microprocessor 20, via the internal bus 29, for use in combination with a firmware program 22 to aid in calculating the fluid density passing through the pipeline 8.

The output signal from the flowmeter 4 is applied to a counter and control logic circuit 24. This circuit measures the flowmeters frequency signal by calculating the reciprocal of its time interval and subsequently produces a corresponding digital signal. The digital signal is then applied to the microprocessor 20, via the internal bus 29, to serve as one of the parameters used with the firmware program to calculate the flow rate of the fluid.

The instrument package also includes a RAM 25 and a ROM 27 that are accessed by means of the internal bus 29. The RAM is used to store the variables of the firmware program 22; the ROM stores the system control programs and other computational data related to cryogenic fluids and formula constants.

The two remaining elements of the instrument package 16 is a bus buffers and control logic circuit 31 and a regulated power supply 35. The circuit 31 interfaces with the internal bus 29 and is used for receiving and controlling a selected plurality of external devices i.e., meters and display devices. The power supply 35 is designed to provide and condition the required power to operate the system.

Figure 4:
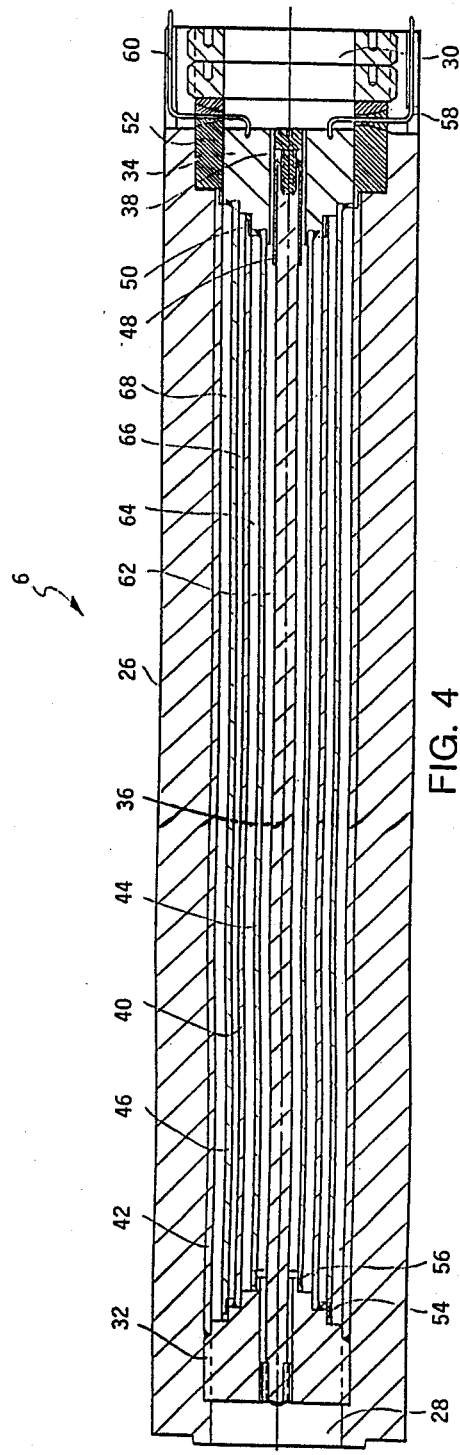
FIG. 4 is a vertical section through the Dielectric-to-Density Converter (DDC) of the measuring system of FIG. 1.

The DDC sensor is preferably of the form shown in FIG. 4. As shown, the DDC 6 has tubular housing 26 which is open at each end, as seen at 28 and 30. Stepped electrodes 32 and 34 are mounted within the housing 26 adjacent the respective ends 28 and 30. The stepped electrodes 32 and 34 are secured together by a central shaft 36 retained by a suitable shaft screw 38, and serve to support a plurality of cylindrical electrodes 40, 42, 44 and 46. Shaft 36 is electrically connected to stepped electrode 32 but is insulated from stepped electrode 34 by an insulating sleeve 48. Similarly, cylindrical electrodes 40 and 42 are electrically connected to stepped electrode 32 but are insulated from stepped electrode 34 by insulators 50 and 52. Conversely, cylindrical electrodes 44 and 46 are electrically connected to stepped electrode 44 and 46 but are insulated from stepped electrode 32 by insulating rings 54 and 56. Conductor 58 connects housing 26, stepped electrode 32, shaft 36 and cylindrical electrode 40 and 42 to ground or a source of lower potential. On the other hand, conductor 60 connects stepped electrode 34 and cylindrical electrodes 44 and 46 to a source of higher potential. In this way, shaft 36 and the cylindrical electrodes 40, 42, 44 and 46 form a plurality of concentric capacitors, whose capacitance is determined by the dielectric characteristics of the fluid passing through the spaces 62, 64, 66 and 68 between the respective pairs of electrodes. Conductors 58 and 60 are also connected to supply electrical signals, indicative of the sensed capacitance, to the capacitance sensing circuit seen at 70 in FIG. 2 and shown in greater detail in FIG. 4.

THE DESIGN OF THE DIELECTRIC-TO-DENSITY SENSOR

The DDC sensor 6 design is approached from a combination of sensing, fluid dynamic and safety standpoints in view of its application with a fluid such as hydrogen which can become hazardous. The DDC sensor consists of a set of three or more pairs of concentric conducting cylinders forming a set of parallel capacitors. Thus, shaft 36 cooperates with cylindrical electrode 44 to form a first capacitor, while cylindrical electrode 44 also cooperates with cylindrical electrode 40 to form a second capacitor. Similarly, cylindrical electrode 40 cooperates with cylindrical electrode 46 to form a third capacitor and electrode 46 cooperates with electrode 42 to form a fourth capacitor. The inter-cylinder spaces 62, 64, 66 and 68 are filled by the dielectric fluid with a capacitance, or dielectric constant $\epsilon$. For each pair of cylinders the capacitance per unit length is give by:

$$C = \frac{2\pi\epsilon}{\mathrm{Ln}(r_a/r_b)}$$

where $r_a$ is the outer radius of the inner cylinder, carrying a charge $+Q$ per unit length; and, inner radius $r_b$ of the outer cylinder, carrying a charge $-Q$ per unit length; or vice versa. The dielectric constant $\epsilon$ is thus given by:

$$\epsilon = C_x/C_0$$

where $C_o$ is the DDC capacitance under vacuum condition. Note the potential difference is derived from the Gauss electric flux theorem as follows:

$$V_a - V_b = -\frac{Q}{2\pi\epsilon}\int_b^a \frac{dr}{r} = -\frac{Q}{2\pi\epsilon}\mathrm{Ln}\left(\frac{r_a}{r_b}\right)$$

and $$E = -\frac{\partial V}{\partial r} = \frac{Q}{2\pi\epsilon r}$$

where r is the radius, and E is the electric field intensity.

The above derivations on electric potential and field intensity provide useful design reference when dealing with low temperature effect, particularly, for potentially hazardous fluid operation, such as with supercritical hydrogen in gaseous or condensed matter state. $\partial V/\partial r$ should then be kept within a safe ratio in relation to the ionization potential in order to eliminate any chance for dielectric breakdown; but, conducive to sensitive measurement.

In consideration of the fluid dynamic effect on dielectric distribution, the respective diameters of the cylindrical electrodes are designed, such that, in conjunction with their supporting flow straighteners, the sectional through-flow areas have the same hydraulic diameter. The purpose is to enable the fluid velocities entering and leaving the separate inter-cylinder space to achieve essentially the same flow velocity profile during the fluid transitional process.

THE CAPACITANCE MEASURING CIRCUIT

Figure 3:
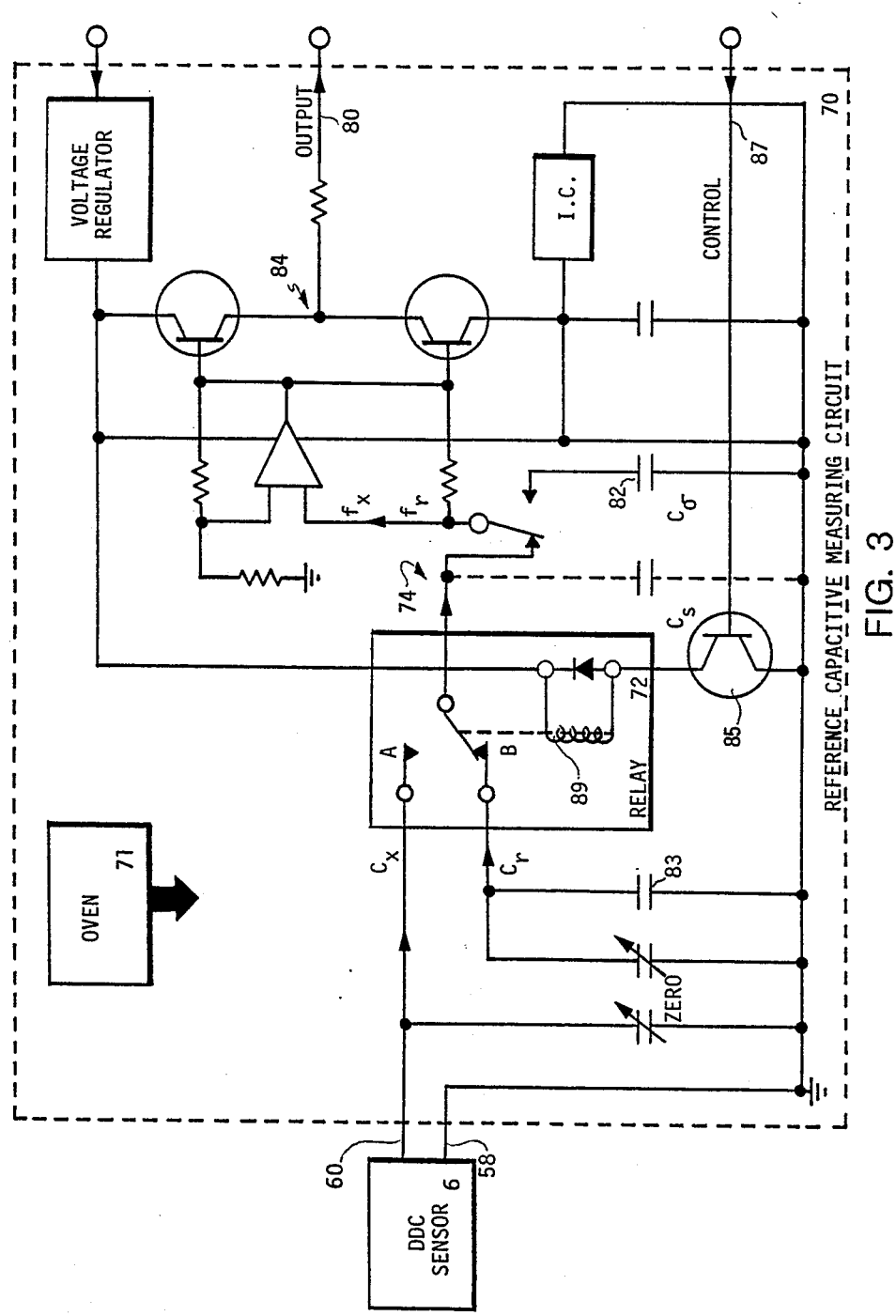
FIG. 3 is a circuit diagram of the capacitance sensing means of the measuring system of FIG. 1.

As noted above, conductors 58 and 60 of the DDC sensor 6 are also connected to supply electrical signals, indicative of the sensed capacitance, to the capacitance measuring circuit 70 as shown in block form in FIG. 2 and in greater detail in FIG. 3. As seen in FIG. 3, the capacitance measuring circuit is of a referenced oscillator design which is capable of generating frequency outputs that can be digitized into a capacitance measurement. The capacitance $C_x$, which is sensed by the DDC sensor 6 and supplied to the measuring circuit 70 by conductors 58 and 60, is supplied through contact A of relay 72 to a referenced oscillator circuit 74 and switching circuit 84. These circuits are designed to produce a sensed frequency $f_x$ on output conductor 80 and, hence, to the DDC converter seen at 86 in FIG. 2.

At the same time, the $f_x$ signal due to the DDC sensor 6 is continuously being referenced to a known reference frequency $f_r$, produced in the oscillator circuit 74. The reference frequency is generated when contact B of relay 72 is closed, and when the relay is connected to a high stability reference capacitance $C_r$, shown at 83, which has a precisely known capacitance value. The value of $C_r$ can be chosen, so that $C_r = C_o$ and, the signal $f_r$ (across capacitor 83 from transistor 85) can be set at a known frequency such as 500 KHz. Since the frequency and capacitance relationship in an oscillator circuit, such as oscillator 74, is known precisely in theory, accurate and stable determination of $C_x$ can be made by ratiometric methods with high resolution. The operation of relay 72 is controlled by signals supplied from a suitable timing circuit not shown, through conductor 87 and transistor 85 and is preferably designed to provide three readings of $f_x$ for each reading of $f_r$. Numerous forms of switching circuits are well known and the details of switching circuit 82 do not form a part of the present invention. To maintain a drift-free capacitance measurement, the operating environment of the measuring circuit 70 is preferably maintained at a constant temperature by an oven 71 as also depicted in FIG. 4.

Although the referenced oscillator described above is the preferred form of the present invention, it will be apparent to those skilled in the art that other circuits could be used to accomplish the capacitance measurement. Thus, for example, an auto-balancing three-terminal capacitance bridge with a digital converter could be referenced in a manner similar to the referenced oscillator described above. Such alternatives are well known in the art and are considered to be within the scope of the present invention.

DIFFERENTIAL CAPACITIVE MEASUREMENT

When the signal from the DDC sensor 6 appears on conductors 58 and 60 in FIG. 3 and is switched by relay 72 into the switching circuit 84, the resultant frequency $f_m$ is determined by the capacitance $C_x$ sensed by the DDC sensor 6, a bias capacitor $C_b$ and the stray capacitance $C_s$ due to circuit wiring. Together, these aggregate into $C_m$ where $$C_m = C_x + C_b + C_s$$

Further introducing $C_o$, as the "base value", we have during the fluid measurement:

$$C_x = C_0 + \Delta C_x$$

$C_x = C_0$ and $\Delta C_x = 0$ only when $\epsilon = 1$; namely, at an initial condition when the DDC sensor is assumed to be under vacuum condition in the absence of $C_S$. The value of $C_o$ is known from laboratory calibration of the sensor and is stored in a RAM 25 for use with the microprocessor 20 and is available for recall, as needed, by the DDC converter 86. Thus, the variation of $f_m$ is totally determined by $C_x$.

Since $$f_m \propto \frac{1}{RC_m}$$

and $$f_r \propto \frac{1}{RC_r}$$

The value of $C_m$ is computed from the measured frequencies and the known $C_r$ value:

$$C_m = \left[\frac{f_r}{f_m} \cdot C_r\right] \times \text{Const.}$$

Note that $C_m \neq C_x$. However, any change in $C_m$ will be entirely due to change in $C_x$ from $C_o$ which is the known base value when no fluid is in the DDC sensor 6.

Although, strictly speaking, $\epsilon = 1$ only occurs when the capacitive sensor is under vacuum: the computing measurement is designed so that under this standard $C_o$ condition, the indication of $C_m$ is nulled to read 0 through adjustments or algorithm. Any subsequent change from this null reading, e.g., under cryogenic measurement condition, is a measurement of $\Delta C_x$. Thus, in the measurement of cryogenic fluid density; and, in the determination of the void ratio or quality factor, the measurement is confined only to this $\Delta C_x$ value.

THE BASE VALUE OF $C_o$ AND THE EFFECT OF STRAY CAPACITANCE $C_s$

In a system designed for cryogenic application, when the operating electronic circuit cannot be located immediately adjacent to the sensor, wiring and cable can introduce significantly stray capacitance $C_s$.

To account for the effect due to $C_s$, the basic capacitance value $C_o$ of the DDC sensor 6, namely, the capacitance at $\epsilon = 1$, is first calibrated in the laboratory with a capacitance bridge. This value is either measured with the DDC sensor 6 in a high vacuum environment; or, in dry air at known pressure and temperature, with the precise dielectric constant value $\epsilon_0$ of air obtained by correcting for the effects due to atmospheric pressure and temperature. Since the dielectric constant of the reference fluid must be knwon precisely; liquid dielectric, such as $C_6H_6$ (benzene) with $\epsilon = 2.284$ at 20° C. can be used as the calibration reference. However, it was found that the actual dielectric properties of reference fluid may vary from their published standard values. The availability of high accuracy instruments for the measurement of dielectric constants of liquid media provides greater precision and reduces the uncertainties. The instrumentation reported by R. N. Jones and L. E. Huntly of the U.S. National Bureau of Standards is able to yield uncertainties of ±0.01%. Together with the comprehensive survey by A. F. Dunn of National Research Council, Canada, these publications provide valuable references to the high degree of precision capable of being calibrated by standard laboratories.

In view of possible effect due to low temperature expansion coefficient, which is small for cylindrical capacitors, the DDC sensor 6 can be immersed in cryogenic fluids at known temperatures for test at known dielectric constants of the fluids: the effect to $C_o$ is then determined for the operating temperature range.

If there is no stray capacitance, the actual capacitance of the DDC 6 in cryogenic fluid is given by $C_x$ and $$\Delta C_x = C_x - C_0$$

The differential value of $\Delta C_x$ is now the key measurement quantity. Although the amount of stray capacitance $C_s$ is not always known precisely, the referenced capacitive measuring circuit 70 is designed to allow a null adjustment of $C_d$ at operating temperature and pressure condition; so that $C_d$ becomes $$C_d = C_0 + C_s + C_b$$

whereas $C_d$ represents only a null-adjustment datum value, on the assumption that $\epsilon$ is virtually equal to 1. An adjustable capacitive trimmer in the circuit 70 provides an amount of bias adjustment equal to $C_b$ for balancing out the residual small difference.

REAL-TIME COMPUTATION OF CRYOGENIC FLUID DENSITY

Once the setting is made, the subsequent DDC operation is transformed into the measurement and computation based only on $\Delta C_x$ and $C_o$ which is a known value. Real-time knowledge of $C_m$ and $C_d$ are no longer needed. The value of $\Delta C_x$ is almost entirely due to the change of the dielectric constant $\epsilon_x$ of the cryogen from its datum value of $\epsilon = 1$; assuming that there is no variation in stray capacitance due to temperature effect, in which case $$\Delta C_x = C_m - C_d = C_x - C_0$$

The value of the cryogenic density $\rho$ is derived from the following computations:

$$\epsilon_x = \frac{[C_0 + \Delta C_x]}{C_0} = 1 + \frac{\Delta C_x}{C_0}$$

The $\epsilon_x - 1$ function derived into the following form $$\epsilon_x - 1 = \frac{\Delta C_x}{C_0}$$

The Clausius-Mossotti function (CMR) is given by $$\frac{(\epsilon_x - 1)}{(\epsilon_x + 2)} = \frac{\Delta C_x}{[\Delta C_x + 3C_0]}$$

Based on $\epsilon_x - 1$ calculated from dielectric measurement, $\kappa$ is determined by:

$$\kappa = A(0) + A(1)[\epsilon_x - 1] + A(2)[\epsilon_x - 1]^2 +$$

$$A(3)[\epsilon_x - 1]^3 + \ldots = \Phi(\epsilon - 1) = A(0) + A(1)\left[\frac{\Delta C_x}{C_0}\right] +$$

$$A(2)\left[\frac{\Delta C_x}{C_0}\right]^2 + A(3)\left[\frac{\Delta C_x}{C_0}\right]^2 + \ldots$$

As given previously, the values of A(0), A(1), A(2), A(3), and A(4) are known coefficients of the polynominal equation for the fluid, which are determined from iteration based on published values of the density and dielectric constant relationship of the cryogenic fluid.

The density $\rho$ of the cryogenic fluid is thus given by $$\rho = \kappa \left[\frac{\epsilon - 1}{\epsilon + 2}\right] = \Phi(\epsilon - 1) \cdot \left[\frac{\Delta C_x}{\Delta C_x + 3C_0}\right]$$

with all computed values based solely on the measurement of $\Delta C_x$; since $C_o$ is a constant of known value. The use of a differential capacitance value of $\Delta C_x$ and $C_o$ avoids the problems related to the grounding effects in capacitive measurement and electronic design. In space operation, unlike on earth when one can refer to "ground", the latter becomes an anomaly in terminology and in technique.

REFERENCED AUTOMATIC NULL CORRECTION FOR STRAY CAPACITANCE CHANGE

The change of stray capacitance due to low-temperature circuit, material, and wiring variables may lead to significant measurement error, if not accounted for. This often takes the form of slow time-varying drift, which is difficult to anticipate, or to correct by a fixed-value null pre-set. To compensate for such effects, the capacitive measurement circuit 70 provides a temperature-stabilized capacitance $C_o$ as a comparative standard. When switched in to read $f_r$ during the referencing cycle, any change in stray capacitance $C_s$ is immediately noticeable through the shift in frequency ratio, or capacitive difference. The corresponding change in $C_s$ is placed in the RAM 25 memory and then is transformed by the microprocessor 20 into real-time null adjustment to offset the stray capacitance variation.

As $C_x$ and $C_r$ are both subject to the effect of stray capacitance $C_s$. Hence, an additional sampling reference capacitance $C_\sigma$ of precisely known value seen at 82 in FIG. 3, is used to provide the aforementioned corrective function.

The frequency ratio ($\theta$) due to $C_\sigma$ and $C_r$ is given by $$(\theta) = \frac{f_r}{f_\sigma} = \frac{C_\sigma}{[C_r + C_s]}$$

Thus, the value $$C_s = \frac{C_\sigma - (\theta)C_r}{\theta}$$

can be readily determined for the automatic compensation of stray capacitance variables.

COMPUTATION OF DIELECTRIC PARAMETERS AND DENSITY

Following the null process, the computations for relevant dielectric parameters and fluid density are processed as follows:

| $\Delta C_x$ | $\epsilon + 2$ | $\epsilon - 1$ | K | $(\epsilon - 1)/(\epsilon + 2) = $ CMR | $\rho$ |
|---|---|---|---|---|---|
| (pF) | $= \frac{\Delta C_x + 3C_0}{C_0}$ | $= \Delta C_x/C_0$ | $\Phi(\epsilon - 1)$ | $= \frac{\Delta C_x}{\Delta C_x + 3C_0}$ | K · CMR |

SYSTEM PERFORMANCE

FIG. 1 illustrates the instant invention in a system defined for liquid hydrogen mass flow transfer and fluid state diagnostic functions. The flow meter 4 and the DDC sensor 6 are designed to be insertable into the pipeline 8 and the system 2 with the instrument package 16 providing digital display and real-time output of the fluid density and $\Delta C_x$ measurements; computing with volumetric flowrate, it yields the mass flowrate and totalized mass flow transfer.

For hydrogen measurement and diagnostics, the DDC sensor 6 is capable of providing density measurements ranging from supercritical, through subcritical to slush hydrogen phases. Through the sensing of fluid density, its ability to quantify the mixed-phase flow in terms of void ratio or quality factor has also been confirmed. Solid formation in hydrogen at temperature below 14° F., and down to 10° K., becomes detectable; while above 20° K. to 21° K., the density-bifurcation phenomena during phase transition from liquid to vapor phase have been observed. The real-time digital-to-analog output of the DDC sensor 6 enables it to monitor dynamic and unsteady phenomena during phase changes and in the supercritical regime.

The resolution of hydrogen density measurement is determined as $5 \times 10^{-4}$ F.S., capable of detecting very small density variations. The uncertainty of $LH_2$ density measurements is estimated conservatively as $2 \times 10^{-3}$ of reading and for liquid oxygen at $1 \times 10^{-3}$ of reading.

When the density measurement of the DDC sensor 6 is computed in conjunction with the output of a high precision cryogenic flowmeter 4 the mass flow measurement of $LH_2$ achieves a precision of 0.03 percent based on weight-time calibration.

Figure 5:
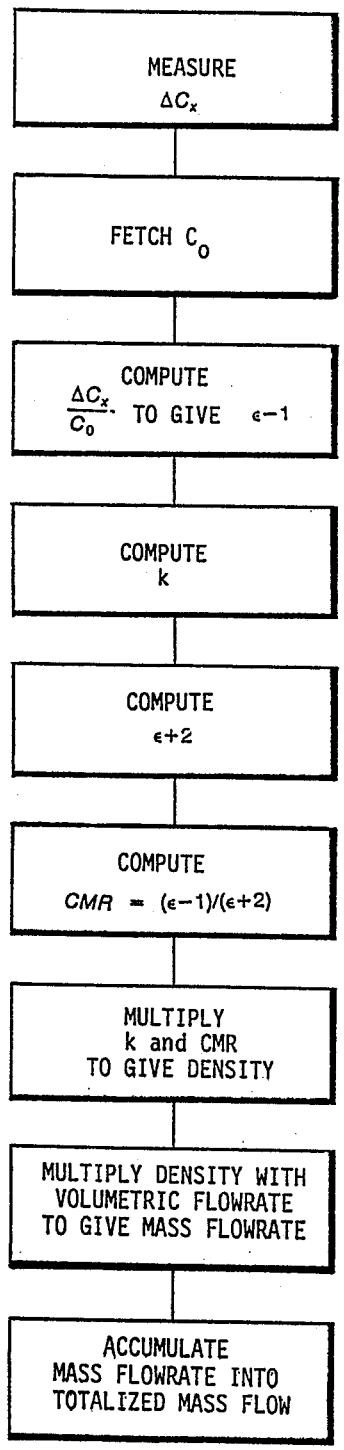
FIG. 5 is a flow diagram showing the steps of the software program of the microprocessor of the measuring system of FIG. 1.

To facilitate understanding the operation of the flow measuring system, FIG. 5 is included to provide a step-by-step flow diagram of the operation. As shown, DDC sensor 6 measures the capacitance $C_x$ of the fluid flowing through the pipeline 8 of FIG. 1. This value is passed through the capacitance measuring circuit 70 of FIGS. 2 and 4 to the DDC converter 86 of FIG. 2. The microprocessor 20 through interaction with the RAM 25 and ROM 27 takes the value of $C_x$ from the DDC converter 86, retrieves the stored value of $C_o$ and computes $\Delta C_x/C_0$ to give $\epsilon - 1$ using Equation 13 above. Next, the microprocessor 20 computes the value of k from Equation 9 above and computes the values of $\epsilon + 2$ from Equation 14 above. With this information, the microprocessor 20 can then compute CMR using the Clausius-Mossotti equation. The microprocessor 20 then multiplies k by CMR to give the density of the fluid in the pipeline 8, multiplies the density by the volumetric flowrate measured by flowmeter 4 to give the mass flowrate and accumulates the mass flowrate to provide the totalized mass flow. The microprocessor 20 then causes the values for the density, volumetric flowrate, mass flowrate and the totalized mass flow to be displayed by the instrument package 16.

One of the research directed purposes of the invention is to provide for the experimental investigation in a less known field of cryogenic fluid dynamic, particularly, on the study of the motional phenomena and the related changes in low-temperature fluid state. For stationary fluids, such as liquid hydrogen in a bubble chamber, the evaluation of whether the particle beam and particle trajectories can induce fluid state change and other interactions, requires instrumentation capable of being justified on theoretical ground. As shown by the previous analysis, only through conceptual rigor in design can the instrument provide investigators with objective phenomenological understanding, as well as quantitative evaluation capability. On the other hand, the concept of the instant invention, which is based on a molecular model, applies the macroscopic concept on a microscopic scale according to the present state of knowledge. The interplay between theories and conceptualized engineering is shown through the present design. The differential dielectric measurement method offers important improvements to cryogenic fluid measurements under space conditions. By using $\Delta C_x$ and $C_o$, the reliance on $C_x$ measurement used in prior arts is avoided. $C_x$ is more susceptable to the ground, or earth, condition; whereas in space the word of electric ground becomes itself anomalous.

In summary, one of the major contributions of the invention is that it allows the microprocessor 20 to employ the theoretically rigorous molecular dielectric equation by the quantitation of the susceptibility parameter k. This quantitation bridges the gap between the molecular and macroscopic equation. The microprocessor 20 also employs the theoretically rigorous molecular Clausius-Mossotti equation, rather than the less rigorous macroscopic equation, in computing the density and mass flow of a cryogenic fluid. This computation also includes the use of all pertinent dielectric parameters, such as the polarizability and susceptibility parameters.

While the invention has been described in complete detail and pictorially shown in the accompanying drawings it is not to be limited to such details, since many changes and modifications may be made to the invention without departing from the spirit and the scope thereof. For example, various forms of flowmeters may be substituted for the flowmeter 4 of FIG. 1. Moreover, numerous alternative circuits may be found for the capacitance measuring circuit shown at 70 in FIG. 2. In addition, numerous other variations and modifications may be made without departing from the present invention. Hence, it is described to cover any and all modifications and forms which may come within the language and scope of the claims.

We claim:

1. A cryogenic density and mass-flow measurement system for accurately determining the characteristics and mass flow rate of a cryogenic fluid over a wide range of fluid states ranging from supercritical through subcritical phases; said system comprising:
    (a) differential capacitance measuring means having at least one pair of electrodes with space therebetween for receiving said fluid;
    (b) flowmeter means positioned to measure the volumetric flowrate of said fluid, and
    (c) microprocessor means receiving signals from said differential capacitance measuring means and from said flowmeter and serving to compute the density and mass flow of said fluid from said signals wherein said microprocessor employs the theoretically rigorous molecular dielectric equation by the quantitation of the susceptibility parameter k which bridges the gap between the molecular and macroscopic equation where said molecular dielectric equation is in the form of:

$$\rho = \kappa[(\epsilon - 1)/(\epsilon + 2)],$$

$$\kappa = A(0) + A(1)(\epsilon-1) + A(2)(\epsilon-1)^2 + A(3)(\epsilon-1)^3 + \ldots = \Phi(\epsilon-1)$$

where:
- $\rho$ = density of cryogenic fluid
- $\epsilon$ = dielectric constant
- $\Phi$ = function of, and A(0) through A(3) are known coefficients of the polynominal equation for the fluid, and are determined from iteration based on published values of the density and dielectric constant relationship of the fluid.

2. The system of claim 1 wherein the molecular equation further comprises the following polarizability and susceptibility parameters respectively:

Susceptibility Parameter:

$$\kappa = A(0) + A(1)(\epsilon-1) + A(2)(\epsilon-1)^2 + A(3)(\epsilon-1)^3 + \ldots = \Phi(\epsilon-1)$$

Polarizability:

where $$\kappa = W/p,$$

But $$\epsilon - 1 = \gamma\chi = \gamma N(\alpha + \mu^2/3KT),$$

where $\mu$ is a dipole moment parameter. Accordingly, $(\epsilon-1)$ is a parameter directly related to dielectric susceptibility $\chi$, $\kappa$ is, thus, interpreted as a function of the dielectric susceptibility $(\epsilon-1)$,
where:
- $\epsilon$ = dielectric constant
- $\Phi$ = function of
- W = molecular weight
- p = molecular polarizability
- $\gamma$ = proportional constant
- $\chi$ = dielectric susceptibility, and
- A(0) through A(3) are the coefficients of the polynominal equation, which are determined with the dielectric and thermophysical properties of said fluid.

3. The system of claim 1 further comprising a firmware program that operates in combination with said microprocessor to control the sequence of operation of said system.

4. The system of claim 1 wherein said molecular Clausius-Mossotti equation, as distinct from the macroscopic Clausius-Mossotti equation, employs the value $$\rho = \Phi(\epsilon - 1)\left[\frac{\epsilon - 1}{\epsilon + 2}\right],$$

where $\Phi[\epsilon - 1] = A(0) + A(1)[\epsilon - 1] + A(2)[\epsilon - 1]^2 + A(3)[\epsilon - 1]^3 + \ldots$ which bridges the conceptual gap between the macroscopic dielectric theory and that of the more rigorous molecular dielectric theory where A(0), A(1), A(2), A(3) and A(4) are equation coefficients determined with measurable dielectric parameters; and in reference to the thermophysical properties of said fluid, such as obtainable from the National Bureau of Standards publications by Younglove et al, whereas the parameter $\epsilon_x - 1$ is determined by computing the ratio of $\Delta C_x/C_0$, where $\Delta C_x$ is a measured differential quantity and $C_0$ is a known quantity $$\epsilon_x - 1 = \frac{\Delta C_x}{C_0}$$

and, the Clausius-Mossotti raatio is also calculated as a function of $\Delta C_x$ and $C_0$ as follows:

$$\frac{(\epsilon_x - 1)}{(\epsilon_x + 2)} = \frac{\Delta C_x}{[\Delta C_x + 3C_0]}$$

and where the fluid density is determined as a product of k and Clausius-Mossotti ratio as follows:

$$\begin{aligned}
\rho &= \kappa[(\epsilon - 1)/(\epsilon + 2)] \\
&= \Phi(\epsilon - 1)[\Delta C_x/(\Delta C_x + 3C_0)], \\
\kappa &= A(0) + A(1)(\epsilon_x - 1) + A(2)(\epsilon_x - 1)^2 + A(3)(\epsilon_x - 1)^3 + \ldots = \Phi(\epsilon - 1) \\
&= A(0) + A(1)\left(\frac{\Delta C_x}{C_0}\right) + A(2)\left(\frac{\Delta C_x}{C_0}\right)^2 + A(3)\left(\frac{\Delta C_x}{C_0}\right)^3 + \ldots
\end{aligned}$$

The coefficients A(0), A(1), A(2), A(3) are of known values.

5. A cryogenic density and mass-flow measurement system for accurately determining the characteristics of a cryogenic fluid over a wide range of fluid states ranging from supercritical through subcritical phases; said system comprising:

A. differential capacitance measuring means having at least one pair of electrodes with space therebetween for receiving said fluid; wherein said differential capacitance measuring means comprises:
  (a) plurality of concentric, open-ended cylinders, and
  (b) first and second electrodes supporting respective ends of said cylinders in concentric spaced relation, said first electrodes being electrically connected to alternate ones of said cylinders, said second electrode being electrically connected to the remainder of said cylinders, B. flowmeter means positioned to measure the volumetric flowrate of said fluid, and C. microprocessor means receiving signals from said capacitance measuring means and from said flowmeter and serving to compute the density and mass flow of said fluid from said signals.

6. A cryogenic density and mass-flow measurement system for accurately determining the characteristics of a cryogenic fluid over a wide range of fluid states ranging from supercritical through subcritical phases; said system comprising:

(a) differential capacitance measuring means having at least one pair of electrodes with space therebetween for receiving said cfluid where said means comprises a plurality of concentric, open-ended cylinders wherein for each cylinder pair the capacitance per unit length is determined by the following formula:

$$C = \frac{2\pi\epsilon}{Ln(r_a/r_b)}$$

where:
c = capacitance per unit length
$r_a$ = outer radius of the inner cylinder carrying a charge +Q per unit length,
$r_b$ = inner radius of the outer cylinder carrying a charge −Q per unit length,
$\epsilon$ = dielectric constant given by:

$\epsilon = C_x/C_0$ where:
$c_x$ = DDC capacitance
$c_0$ = DDC capacitance under vacuum condition,
  (b) first and second electrodes supporting respective ends of said cylinders in concentric spaced relations, said first electrodes being electrically connected to alternate ones of said cylinders, said second electrode being electrically connected to the remainder of said cylinders,
  (c) flowmeter means positioned to measure the volumetric flowrate of said fluid, and
  (d) microprocessor means receiving signals from said capacitance measuring means and from said flowmeter and serving to compute the density and mass flow of said fluid from said signals.

7. A cryogenic density and mass-flow measurement system for accurately determining the characteristics of a cryogenic fluid over a wide range of fluid states ranging from spercritical through subcritical phases; said system comprising:
  A. capacitance measuring means having at least one pair of electrodes with space therebetween for receiving said fluid;
  B. flowmeter means positioned to measure the volumetric flowrate of said fluid, and
  C. microprocessor means that receives signals from said capacitance measuring means and from said flowmeter where said microprocessor;
     (a) stores the value of capacitance of said capacitance measuring means when no fluid is in the spaces between said electrodes,
     (b) compares said stored value of capacitance with the value measured by said capacitance measuring device,
     (c) employs the molecular Clausius-Mossotti equation in computing the density of said fluid from said stored and measured capacitance values, and
     (d) computes the mass flow of said fluid from said computed density and the flowrate measured by said flowmeter.

8. A cryogenic density and mass-flow measurement system used in combination with a cryogenic fluid storage container delivering the fluid through a pipeline to a fuel receiving vehicle, wherein said system comprises:
  A. a flowmeter, connected in-line within the pipeline in the path of the cryogenic fluid where said flowmeter has the means for measuring the volumetric flow rate of the fluid and to provide a flow rate output signal,
  B. a dielectric-to-density converter (DDC) sensor, connected in-line within the pipeline in the path of the cryogenic fluid, where said DDC has the means for continuously measuring the fluid density of the cryogenic fluid flowing in the pipeline and to provide a DDC capacitance ($C_x$) output signal indicative of fluid density, and
  C. an instrument package located external to the pipeline and having an electronics section that functions in combination with a microprocessor and firmware program to receive and process the output signals from said flowmeter and said DDC sensor where said processed signals are used in combination with other parameters to ultimately compute and display flowrate, totalized flow data and mass flow of the cryogenic fluid where said instrument package further comprises:
    (a) an internal bus that provides an interconnection means between selected elements of said instrument package,
    (b) a firmware program,
    (c) a Randon Access Memory (RAM) accesed through said internal bus and that stores the variables of said firmware program,
    (d) a Read Only Memory (ROM) accessed through said internal bus and that stores the system control program and other data related to various fluids and formula constants,
    (e) a microprocessor that functions to process and route data through said internal bus as directed by said RAM, ROM and firmware program,
    (f) a referenced capacitive sensing circuit that receives the DDC capacitance ($C_x$) output signal from said DDC sensor and that includes in part, an oscillator circuit, that functions with two capacitors one of which consists of a DDC capacitor ($C_x$) which is located externally in said DDC sensor and the other is a temperature-controlled reference capacitor $C_r$ having a precisely known capacitance and located within said sensing circuit where said $C_x$ capacitance is periodically compared with said $C_r$ capacitance and where said sensing circuit converts the compared $C_x$ capacitance to a proportional frequency signal,
    (g) a DDC converter circuit that receives the proportional frequency signal from said referenced capacitive sensing circuit and converts the signal to a corresponding digital signal which is then applied to said microprocessor via said internal bus for use in combination with said firmware program to calculate the fluid density,
    (h) a counter and control logic circuit that receives and measures the time interval of the flowrate output signal from said flowmeter and produces a corresponding digital signal which is then applied to said microprocessor via said internal bus for use in combination with said firmware program to calculate the fluid density,
    (i) a bus buffers and control logic circuit that interfaces with said internal bus and used for controlling a selected plurality of external devices, and
    (j) a regulated power supply that produces the required power to operate said system.

9. A cryogenic density and mass-flow measurement system for accurately determining the characteristics of a cryogenic fluid over a wide range of fluid states ranging from supercritical through subcritical phases; said system comprising:
  A. differential capacitance measuring means having at least one pair of electrodes with space therebetween for receiving said fluid; wherein said differential capacitance measuring means comprises:
(a) plurality of concentric, open-ended cylinders where the spaces between said cylinders form equal hydraulic diameter through-flow sections and provide equal distribution of the fluid flowing through said differential capacitance measuring means,
(b) first and second electrodes supporting respective ends of said cylinders in concentric spaced relation, said first electrodes being electrically connected to alternate ones of said cylinders, said second electrode being electrically connected to the remainder of said cylinders, B. flowmeter means positioned to measure the volumetric flowrate of said fluid, and C. microprocessor means receiving signals from said capacitance measuring means and from said flowmeter and serving to compute the density and mass flow of said fluid from said signals.

10. A method for accurately determining the mass flow of a cryogenic fluid over a wide range of fluid states ranging from supercritical through subcritical phases; said method comprising the steps of:
(a) measuring capacitance $C_x$ by means of at least one pair of electrodes having space therebetween for receiving said fluid,
(b) storing the value of capacitance $C_0$ measured by said electrodes when no fluid is in said space; and with which the differential value of $\Delta C_x$ is determined,
(c) computing the density of said fluid from said stored and measured capacitance values by means of the molecular Clausius-Mossotti equation,
(d) measuring the volumetric flowrate of said fluid, and
(e) computing the mass flow of said fluid from said computed density value and the volumetric flowrate.

11. The method of claim 10 comprising the further step of periodically comparing said stored capacitance value with said measured capacitance value.

12. The method of claim 10 wherein said Clausius-Mossotti equation and density relationship employs the value:

$$\kappa = A(0) + A(1)(\epsilon-1) + A(2)(\epsilon-1)^2 + A(3)(\epsilon-1)^3 + \ldots = \Phi(\epsilon-1)$$

and where the required dielectric parameters are calculated from the measured quantities of $\Delta C_x$ and $C_0$ as follows:

$$\epsilon_x - 1 = \frac{\Delta C_x}{C_0}$$

and $$\frac{(\epsilon_x - 1)}{(\epsilon_x + 2)} = \frac{\Delta C_x}{(\Delta C_x + 3C_0)}$$

thus, $$\rho = \kappa((\epsilon - 1)/(\epsilon + 2))$$
$$= \Phi(\epsilon - 1)(\Delta C_x/(\Delta C_x + 3C_0))$$

where:
$\epsilon$ = dielectric constant
$\epsilon_x$ = the change in the dielectric constant from datum value of $\epsilon = 1$
$\Phi$ = function of
$C_x$ = capacitance of the dielectric-to-density converter in cryogenic fluid
$C_o$ = capacitance of the dielectric-to-density converter under a vacuum
$\rho$ = density of cryogenic fluid, and
$A(0)$ through $A(3)$ are the coefficients of the polynomial equation, which are determined with the dielectric and thermophysical properties of said fluid.

13. A method for accurately determining the density of cryogenic fluid over a wide range of fluid states ranging from supercritical through subcritical phases; said method comprising the steps of:
(a) measuring capacitance $C_x$ by means of at least one pair of electrodes having space therebetween for receiving said fluid,
(b) storing the value of capacitance $C_0$ measured by said electrodes when no fluid is in said space, and, with which the differential value $\Delta C_x$ is determined, and
(c) computing the density of said fluid from said stored and measured capacitance values by means of the molecular Clausius-Mossotti equation.

14. The method of claim 13 wherein said molecular Clausius-Mossotti equation and density relationship employs the value $$\kappa = A(0) + A(1)(\epsilon - 1) + A(2)(\epsilon - 1)^2 + A(3)(\epsilon - 1)^3 + \ldots = \Phi(\epsilon - 1)$$

to bridge the theoretical gap between the rigorous molecular dielectric equation and the macroscopic dielectric equation, and where the required dielectric parameters are calculated from the measured quantities of $\Delta C_x$ and $C_0$ as follows:

$$\epsilon_x - 1 = \frac{\Delta C_x}{C_0}$$

and $$\frac{(\epsilon_x - 1)}{(\epsilon_x + 2)} = \frac{\Delta C_x}{(\Delta C_x + 3C_0)}$$

thus, $$\rho = \kappa((\epsilon - 1)/(\epsilon + 2))$$
$$= \Phi(\epsilon - 1)(\Delta C_x/(\Delta C_x + 3C_0))$$

where:
$\epsilon$ = dielectric constant
$\epsilon_x$ = the change in the dielectric constant from datum value of $\epsilon = 1$
$\Phi$ = function of
$C_x$ = capacitance of the dielectric-to-density converter in cryogenic fluid
$C_o$ = capacitance of the dielectric-to-density converter under a vacuum
$\rho$ = density of cryogenic fluid, and
$A(0)$ through $A(3)$ are the coefficients of the polynomial equation, which are determined with the dielectric and thermophysical properties of said fluid.

15. The method of claim 13 comprising the further step of using the dielectric susceptibility function $$\kappa = \Phi(\epsilon - 1)$$

in establishing the relation between fluid density and the Clausius-Mossotti ratio, and which makes possible the determination of fluid density entirely from available capacitance measurement without requiring the knowledge of polarizability, other molecular constants or fluid temperature and pressure in the equation of the state of said fluid as seen from the following equation:

$$\rho = \kappa[(\epsilon-1)/(\epsilon+2)] = \Phi(\epsilon-1)(\Delta C_x/(\Delta C_x + 3C_0)];$$

$$\kappa = A(0) + A(1)(\epsilon_x - 1) + A(2)(\epsilon_x - 1)^2 + A(3)(\epsilon_x - 1)^3 + \ldots$$
$$= \Phi(\epsilon - 1) = A(0) + A(1)(\Delta C_x/C_0) + A(2)(\Delta C_x/C_0)^2 + A(3)(\Delta C_x/C_0)^3 + \ldots,$$

where:
- $\epsilon$ = dielectric constant
- $\epsilon_x$ = the change in the dielectric constant from datum value of $\epsilon = 1$
- $\Phi$ = function of
- $C_x$ = capacitance of the dielectric-to-density converter in cryogenic fluid
- $C_o$ = capacitance of the dielectric-to-density converter under a vacuum
- $\rho$ = density of cryogenic fluid, and
- $A(0)$ through $A(3)$ are the coefficients of the polynomial equation, which are determined with the dielectric and thermophysical properties of said fluid.

16. The method of claim 13 comprising the further step of automatically compensating for stray capacitance effects due to low temperature circuit, material and wiring variables.

17. The method of claim 13 wherein said method is operable to measure the density of said fluid from the supercritical through the subcritical to the slush phase of the cryogenic fluid.

* * * * *